(12) United States Patent
Gibbons et al.

(10) Patent No.: US 9,057,045 B2
(45) Date of Patent: Jun. 16, 2015

(54) METHOD OF LOADING AND DISTRIBUTING CELLS IN A BIOREACTOR OF A CELL EXPANSION SYSTEM

(75) Inventors: David M. Gibbons, Highlands Ranch, CO (US); Brian J. Nankervis, Thornton, CO (US)

(73) Assignee: TERUMO BCT, INC., Lakewood, CO (US)

( * ) Notice: Subject to any disclaimer, the term of this patent is extended or adjusted under 35 U.S.C. 154(b) by 685 days.

(21) Appl. No.: 12/968,483

(22) Filed: Dec. 15, 2010

(65) Prior Publication Data

US 2011/0159584 A1 Jun. 30, 2011

Related U.S. Application Data

(60) Provisional application No. 61/290,629, filed on Dec. 29, 2009.

(51) Int. Cl.
| | |
|---|---|
| *C12N 5/071* | (2010.01) |
| *C12M 1/00* | (2006.01) |
| *C12M 3/00* | (2006.01) |
| *C12M 1/12* | (2006.01) |
| *C12M 3/06* | (2006.01) |

(52) U.S. Cl.
CPC ............... *C12M 29/16* (2013.01); *C12M 23/42* (2013.01); *C12M 23/50* (2013.01); *C12M 25/10* (2013.01); *C12M 25/12* (2013.01); *C12M 27/14* (2013.01)

(58) Field of Classification Search
None
See application file for complete search history.

(56) References Cited

U.S. PATENT DOCUMENTS

| | | |
|---|---|---|
| 3,821,087 A | 6/1974 | Knazek et al. |
| 4,391,912 A | 7/1983 | Yoshida et al. |
| 4,647,539 A | 3/1987 | Bach |
| 4,804,628 A | 2/1989 | Cracauer et al. |
| 4,885,087 A | 12/1989 | Kopf |

(Continued)

FOREIGN PATENT DOCUMENTS

| | | |
|---|---|---|
| EP | 0220650 | 5/1987 |
| GB | 1277544 | 6/1972 |

(Continued)

OTHER PUBLICATIONS

Hoson et al., Evaluation of the three-dimensional clinostat as a simulator of weightlessness, 1997, Planta 203(1): S187-S197 (1997).*

(Continued)

*Primary Examiner* — Robert Yamasaki
(74) *Attorney, Agent, or Firm* — René A. Pereyra; Elizabeth J. Reagan; John R. Merkling

(57) ABSTRACT

A method of distributing a plurality of cells in a bioreactor of a cell expansion system includes manipulating an orientation of the bioreactor such that a net impulse due to gravity acting on the plurality cells in the bioreactor is reduced. One method includes (a) rotating the bioreactor at an angular velocity ω about an axis of rotation and through an angular displacement θ, the bioreactor rotating from a first orientation to a second orientation; (b) holding the bioreactor still at the second orientation for a first period of time $t_1$, wherein $t_1$ substantially equals 2/ω; (c) rotating the bioreactor at the angular velocity ω about the axis of rotation and through the angular displacement θ; and (d) holding the bioreactor still for a second period of time $t_2$, wherein $t_2$ substantially equals $t_1$.

10 Claims, 12 Drawing Sheets

(56) References Cited

U.S. PATENT DOCUMENTS

| | | | |
|---|---|---|---|
| 4,889,812 | A | 12/1989 | Guinn et al. |
| 4,918,019 | A | 4/1990 | Guinn |
| 5,126,238 | A | 6/1992 | Gebhard et al. |
| 5,162,225 | A | 11/1992 | Sager et al. |
| 5,202,254 | A | 4/1993 | Amiot et al. |
| 5,416,022 | A | 5/1995 | Amiot |
| 5,459,069 | A | 10/1995 | Palsson et al. |
| 5,605,822 | A | 2/1997 | Emerson et al. |
| 5,622,857 | A | 4/1997 | Goffe |
| 5,656,421 | A | 8/1997 | Gebhard et al. |
| 5,688,687 | A | 11/1997 | Palsson et al. |
| 5,763,261 | A | 6/1998 | Gruenberg |
| 5,763,266 | A | 6/1998 | Palsson et al. |
| 5,882,918 | A | 3/1999 | Goffe |
| 5,888,807 | A | 3/1999 | Palsson et al. |
| 5,958,763 | A | 9/1999 | Goffe |
| 5,985,653 | A | 11/1999 | Armstrong et al. |
| 5,994,129 | A | 11/1999 | Armstrong et al. |
| 5,998,184 | A | 12/1999 | Shi |
| 6,001,585 | A | 12/1999 | Gramer |
| 6,048,721 | A | 4/2000 | Armstrong et al. |
| 6,096,532 | A | 8/2000 | Armstrong et al. |
| 6,228,635 | B1 | 5/2001 | Armstrong et al. |
| 6,238,908 | B1 | 5/2001 | Armstrong et al. |
| 6,566,126 | B2 | 5/2003 | Cadwell |
| 6,582,955 | B2 | 6/2003 | Martinez et al. |
| 6,642,019 | B1 | 11/2003 | Anderson et al. |
| 6,844,187 | B1 | 1/2005 | Wechsler et al. |
| 6,943,008 | B1 | 9/2005 | Ma |
| 6,979,308 | B1 | 12/2005 | MacDonald et al. |
| 7,041,493 | B2 | 5/2006 | Rao |
| 7,112,441 | B2 | 9/2006 | Uemura et al. |
| 7,172,696 | B1 | 2/2007 | Martinez et al. |
| 7,270,996 | B2 | 9/2007 | Cannon et al. |
| 7,531,351 | B2 | 5/2009 | Marx et al. |
| 7,718,430 | B2 | 5/2010 | Antwiler |
| 2004/0027914 | A1* | 2/2004 | Vrane ............... 366/213 |
| 2006/0019388 | A1 | 1/2006 | Hutmacher et al. |
| 2006/0019391 | A1 | 1/2006 | Marx et al. |
| 2007/0122904 | A1 | 5/2007 | Nordon |
| 2007/0231305 | A1 | 10/2007 | Noll et al. |
| 2007/0298497 | A1 | 12/2007 | Antwiler |
| 2008/0220522 | A1 | 9/2008 | Antwiler |
| 2008/0220523 | A1 | 9/2008 | Antwiler |
| 2008/0248572 | A1 | 10/2008 | Antwiler |
| 2008/0254533 | A1 | 10/2008 | Antwiler |
| 2010/0042260 | A1 | 2/2010 | Antwiler |
| 2010/0105138 | A1 | 4/2010 | Dodd et al. |
| 2010/0144037 | A1 | 6/2010 | Antwiler |
| 2010/0210016 | A1 | 8/2010 | Leuthaeuser et al. |

FOREIGN PATENT DOCUMENTS

| | | |
|---|---|---|
| WO | 8602379 | 4/1986 |
| WO | 90/02171 | 3/1990 |
| WO | 95/04813 | 2/1995 |
| WO | 95/21911 | 8/1995 |
| WO | 97/16527 | 5/1997 |
| WO | 98/53046 | 11/1998 |
| WO | 00/75275 | 12/2000 |
| WO | 2004/090112 | 10/2004 |
| WO | 2007/136821 | 11/2007 |
| WO | 2007/139742 | 12/2007 |
| WO | 2007/139746 | 12/2007 |
| WO | 2007/139747 | 12/2007 |
| WO | 2007/139748 | 12/2007 |
| WO | 2008109674 | 9/2008 |
| WO | 2008/128165 | 10/2008 |
| WO | 2009/034186 | 3/2009 |

OTHER PUBLICATIONS

Infanger et al., Simulated weightlessness changes the cytoskeleton and extracellular matrix proteins in papillary thyroid carcinoma cells, 2006, Cell and Tissue Research 324(2): 267-277.*

International Search Report and Written Opinion issued Dec. 5, 2011 in Application No. PCT/US2010/060409 (PG0203-W001).

Chang et al, "Membrane Bioreactors: Present and Prospects", Advances in Biochemical Engineering, 1991, 44:27-64.

Chang, Ho Nam, "Membrane Bioreactors: Engineering Aspects", Biotech. Adv., 1987, vol. 5, pp. 129-145.

Edgington, Stephen M., "New Horizons for Stem-Cell Bioreactors", Biotechnology, v. 10, Oct. 1992, pp. 1099-1106.

Gastens et al, "Good Manufacturing Practice-Compliant Expansion of marrow-Derived Stem and Progenitor Cells for Cell Therapy", Cell Transplantation, 2007 vol. 16, pp. 685-696.

Gramer et al, "Screening Tool for Hollow-Fiber bioreactor Process Development", Biotechnol. Prog., 1998, 14, 203-209.

Hirschel et al, "An Automated Hollow Fiber System for the large Scale manufacture of mammalian Cell Secreted Product", in Large Scale Cell Culture Technology, ed. Bjorn K. Lydersen, Hanser Publishers, 1987, pp. 113-144.

Nielsen, Lars Keld, "Bioreactors for Hematopoietic Cell Culture", Annu. Rev. Biomed. Eng., 1999,1:129-152.

Pörtner et al, "An Overview on Bioreactor Design, Prototyping and Process Control for Reproducible Three-Dimensional Tissue Culture", in Drug Testing in Vitro: Breakthroughs and trends in Cell Culture Technology, ed. Uwe Marx and Volker Sandig, Wiley-VCH, 2007, Chapter 2, pp. 53-78.

Zhao et al, "Perfusion Bioreactor System for Human Mesenchymal Stem Cell Tissue Engineering: Dynamic Cell Seeding and Construct Development", Biotechnology and Bioengineering, vol. 91, No. 4, Aug. 20, 2005, pp. 482-493.

* cited by examiner

1

METHOD OF LOADING AND DISTRIBUTING CELLS IN A BIOREACTOR OF A CELL EXPANSION SYSTEM

CROSS REFERENCE TO RELATED APPLICATIONS

The present application claims the benefit of U.S. Patent Provisional Patent Application Ser. No. 61/290,629 filed on Dec. 29, 2009, the contents of which are incorporated herein by reference in its entirety.

FIELD

The present disclosure relates to a system and/or method of growing cells in a cell expansion system (CES), and more particularly, a method of loading and distributing cells in a bioreactor of a CES.

BACKGROUND

CESs are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to grow stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems include one or more compartments for growing the cells, such as a cell growth chamber, also referred to herein as a "bioreactor." However, a CES with a stationary bioreactor may limit the production of cells as compared to a system that provides some ability to adjust the position of the bioreactor. For example, the influence of gravity may impede the distribution of cells when first introducing the cells into the bioreactor (also referred to herein as "loading"), and thus the subsequent expansion of cells in the bioreactor. Accordingly, there is a need for a method of loading and distributing cells in a bioreactor associated with a cell expansion system. The present disclosure addresses this and other needs.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

One or more embodiments are generally directed to a method and system for loading and distributing cells in a bioreactor of a cell expansion system. Accordingly, a method of loading and distributing a plurality of cells in a cell expansion system is provided, the method comprising:
  providing a bioreactor;
  orienting the bioreactor in a first orientation; and
  loading the plurality of cells within the bioreactor while:
    rotating the bioreactor around a rotational axis;
    pausing the bioreactor at a second orientation for a first period of time;
    rotating the bioreactor back around the rotational axis to the first orientation; and
    pausing the bioreactor back at the first orientation for a second period of time.

In at least one embodiment the second period of time is substantially equal to the first period of time. In at least one embodiment the bioreactor has a longitudinal axis LA-LA, and when the bioreactor is in the first orientation the longitudinal axis LA-LA is substantially perpendicular to the longitudinal axis LA-LA when the bioreactor is in the second orientation. In at least one embodiment the bioreactor has a longitudinal axis LA-LA, and the longitudinal axis LA-LA is substantially horizontal when the bioreactor is in the first orientation and substantially vertical when the bioreactor is in the second orientation. In at least one embodiment a first angular velocity is maintained while rotating the bioreactor between the first orientation and the second orientation. In at least one embodiment a second angular velocity is maintained while rotating the bioreactor back around the rotational axis to the first orientation, and the second angular velocity is substantially equal to the first angular velocity.

One or more embodiments of the present invention are directed to a multi-phase method of distributing a plurality of cells in a bioreactor of a cell expansion system. Accordingly, a multi-phase timing method of distributing a plurality of cells loaded into a bioreactor of a cell expansion system is provided, the multi-phase timing method comprising:
  a first phase comprising rotating the bioreactor about an axis for a first period of time and through a first angular displacement;
  a second phase comprising holding the bioreactor still for a second period of time;
  a third phase comprising rotating the bioreactor about the axis for a third period of time and through a second angular displacement, wherein the third period of time is substantially equal to the first period of time, and wherein the second angular displacement is substantially equal to the first angular displacement; and
  a fourth phase comprising holding the bioreactor still for a fourth period of time, wherein the fourth period of time is substantially equal to the second period of time.

In at least one embodiment the second period of time is substantially equal to $2\omega^{-1}$, where $\omega$ is an angular velocity (rad/sec) of the bioreactor when rotating the bioreactor during the first phase. In at least one embodiment the first angular displacement is approximately 270°.

In addition to the foregoing, a method of distributing a plurality of cells loaded into a bioreactor of a cell expansion system is provided, the method comprising:
  (a) rotating the bioreactor at an angular velocity $\omega$ about an axis of rotation and through a first angular displacement $\theta_1$, the bioreactor rotating from a first orientation to a second orientation;
  (b) holding the bioreactor still at the second orientation for a first period of time $t_1$, wherein $t_1$ substantially equals $2/\omega$;
  (c) rotating the bioreactor at the angular velocity $\omega$ about the axis of rotation and through a second angular displacement $\theta_2$; and
  (d) holding the bioreactor still for a second period of time $t_2$, wherein $t_2$ substantially equals $t_1$;
  wherein step (a) comes at least before step (b), wherein step (b) comes at least before step (c), and wherein step (c) comes at least before step (d). In at least one embodiment the first angular displacement $\theta_1$ equals approximately 270°. In at least one embodiment a total angular displacement associated with steps (a) and (c) is about 540°.

One or more embodiments of the present invention are directed at manipulating the bioreactor to mitigate the influence of gravity on the distribution of cells in the bioreactor. Accordingly, a method of distributing a plurality of cells in a bioreactor of a cell expansion system is provided, comprising: manipulating an orientation of the bioreactor such that a net impulse due to gravity acting on the plurality cells in the bioreactor is substantially zero. In at least one embodiment said manipulating comprises rotating the bioreactor at a first angular velocity. In at least one embodiment said manipulating further comprises holding the bioreactor substantially stationary for a first period of time $t_1$. In at least one embodiment the first period of time $t_1$ is approximately equal to 2 divided by the first angular velocity (rad/sec). In at least one embodiment said manipulating comprises rotating the bioreactor, and the rotating includes using a plurality of angular velocities. In at least one embodiment said manipulating comprises holding the bioreactor substantially stationary for a period of time $t_p$ equal to 2 divided by the first angular velocity (rad/sec). In at least one embodiment a total angular displacement associated with the manipulating is about 540°.

In at least one embodiment, a method of distributing a plurality of cells in a bioreactor of a cell expansion system is provided, the method comprising: reducing a net impulse due to gravity acting on the plurality of cells by manipulating an orientation of the bioreactor. In addition to the foregoing embodiments noted above, in at least one embodiment said manipulating comprises rotating the bioreactor around at least a first axis of rotation. In at least one embodiment said first axis of rotation is substantially perpendicular to a longitudinal axis LA-LA of the bioreactor. In at least one embodiment said first axis of rotation is substantially coincident with a longitudinal axis LA-LA of the bioreactor.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and is understood by those of ordinary skill in the art to encompass obvious improvements and modifications thereto.

Additional advantages of the embodiments presented herein will become readily apparent from the following discussion, particularly when taken together with the accompanying drawings.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

The drawings are not necessarily to scale.

DETAILED DESCRIPTION

The present disclosure is generally directed to a method for distributing a plurality of cells in a bioreactor of a cell expansion system. As described below, a method of distributing cells within a bioreactor may include loading cells into the bioreactor, rotating the bioreactor, and holding the bioreactor still at certain orientations.

Figure 1:
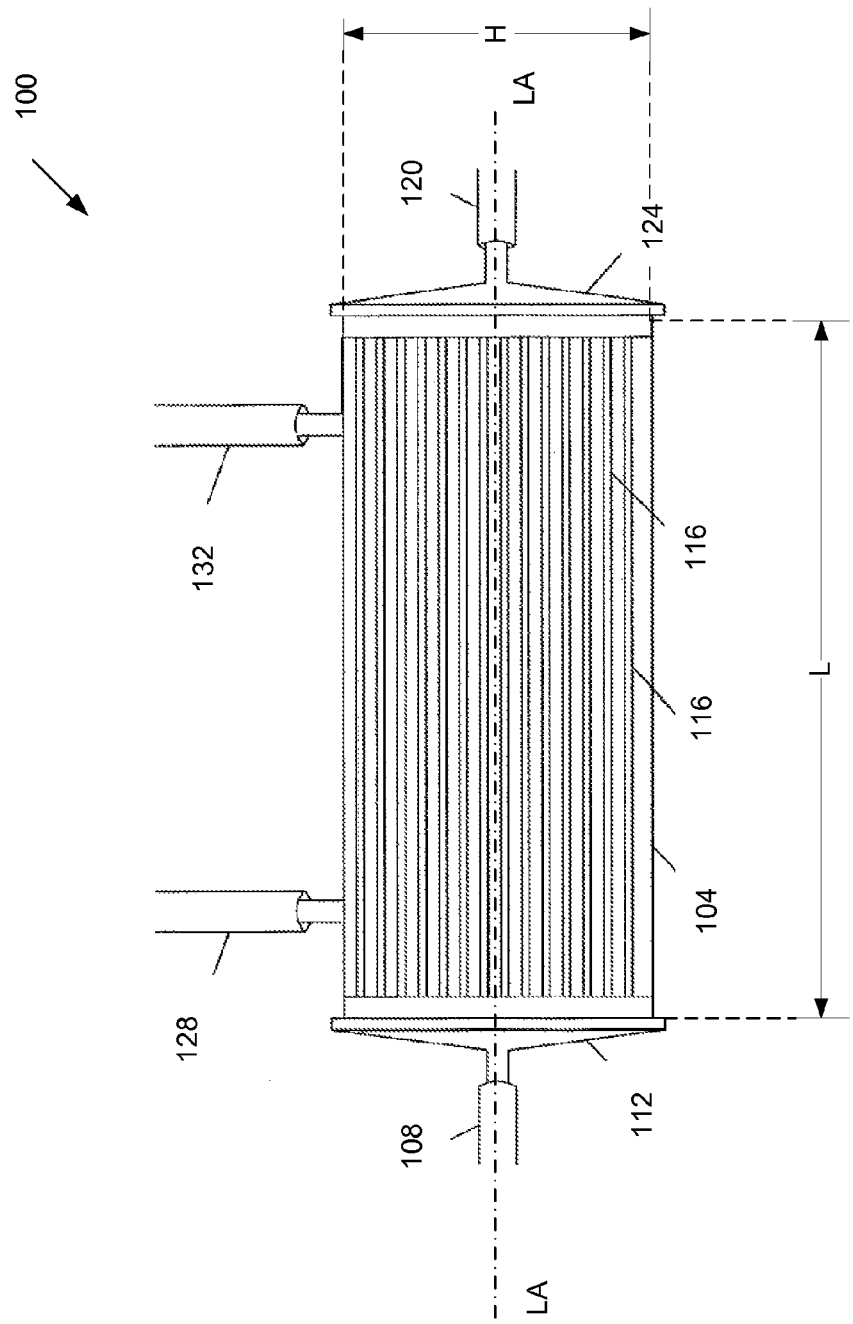
FIG. 1 is a front elevation view of an embodiment of a bioreactor showing circulation paths through the bioreactor.

With reference now to FIG. 1, an example of a bioreactor 100 is shown in front elevation view. Bioreactor 100 has a longitudinal axis LA-LA and includes bioreactor housing 104. In at least one embodiment, bioreactor housing 104 includes four openings or ports: IC inlet port 108, IC outlet port 120, EC inlet port 128, and EC outlet port 132.

Fluid in a first circulation path enters bioreactor 100 through IC inlet port 108 at a first longitudinal end 112 of the bioreactor 100, passes into and through the intracapillary side (referred to in various embodiments as the intracapillary ("IC") side or "IC space" of a hollow fiber membrane) of a plurality of hollow fibers 116, and out of bioreactor 100 through IC outlet port 120 located at a second longitudinal end 124 of the bioreactor 100. Fluid in a second circulation path flows in the bioreactor 100 through EC inlet port 128, comes in contact with the extracapillary side or outside (referred to as the "EC side" or "EC space" of the membrane) of the hollow fibers 116, and exits bioreactor 100 via EC outlet port 132. Fluid entering bioreactor via an EC inlet port 128 is in contact with the outside of the hollow fibers. Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. The media may be replaced as needed. Media may also be circulated through an oxygenator to exchange gasses as needed. Cells can be contained within the first circulation path and/or second circulation path, and can be on either the IC side and/or EC side of the membrane. By way of example and not limitation, specifications for an exemplary bioreactor for use in a cell expansion system are provided in the following table:

TABLE 1

| Specifications for an Exemplary Bioreactor (BioR147A Bioreactor) | | |
|---|---|---|
| 11520 | fibers | fiber count in bioreactor |
| $215 \times 10^{-6}$ | m | fiber ID |

Although bioreactor housing 104 is depicted as cylindrical in shape, it could have a variety of shapes, such as a rectangular cube. Bioreactor housing 104 can be made of any type of biocompatible polymeric material, including a substantially transparent material that permits an observer to see one or more of the plurality of hollow fibers 116, as well as fluid residing within the bioreactor housing 104. Various other bioreactor housings may differ in shape and size.

Figure 2:
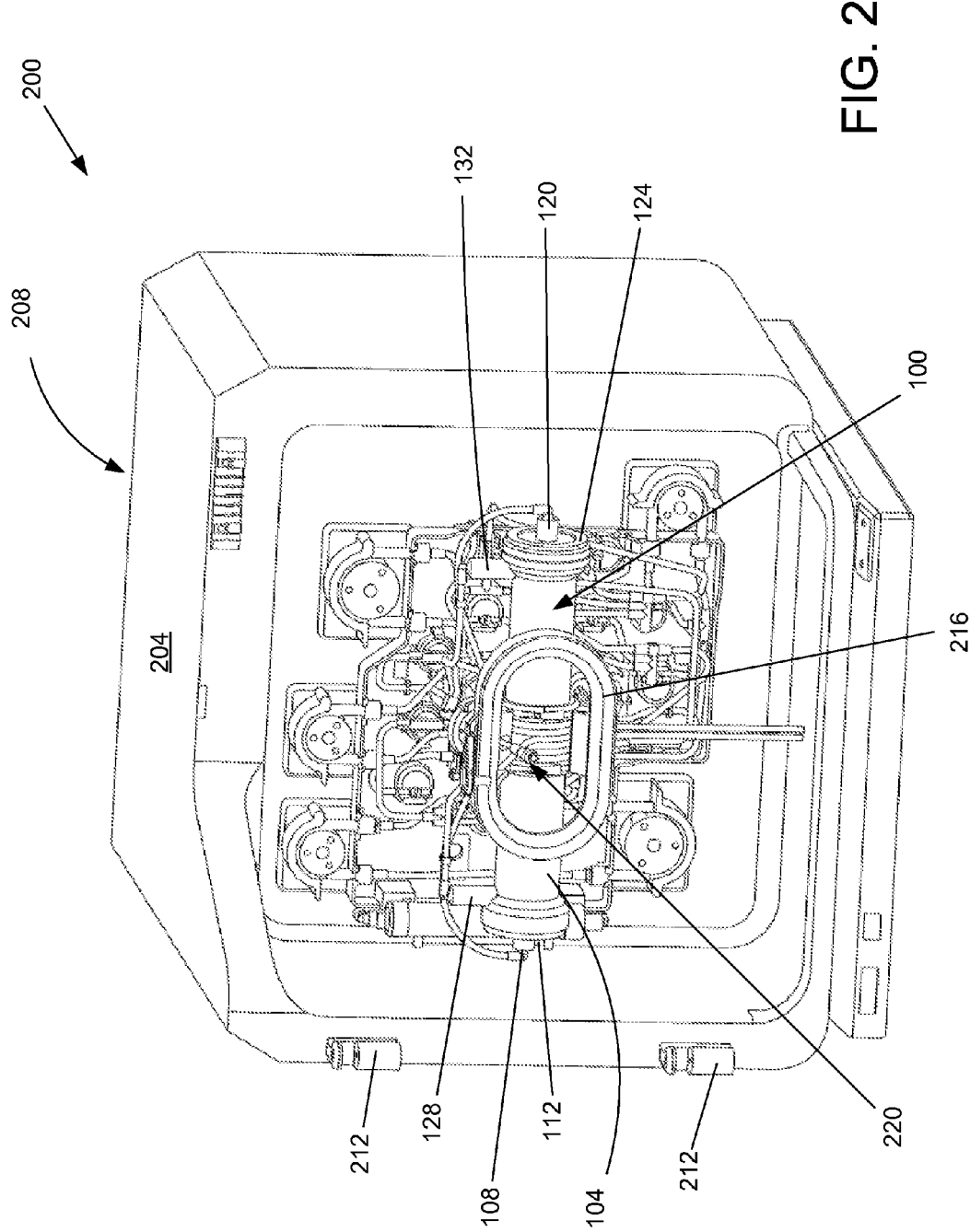
FIG. 2 is a perspective view of a portion of a cell expansion system, including a detachably attached bioreactor.

Referring now to FIG. 2, a portion of a CES 200 is shown in perspective view, and includes a back portion 204 of body 208 of the CES 200. For clarity, the front portion the body 208 is not shown; however, the front portion is preferably attached to the back portion 204, such as by hinges 212, thereby allowing the front portion to comprise a door or hatch that can be opened to access the bioreactor 100 of the CES 200. Attached to the bioreactor 100 may be a spool 216 for tubing and a sampling port 220. The environment in the vicinity of the bioreactor 100 is temperature controlled to provide appropriate conditions for cell growth.

Figure 3:
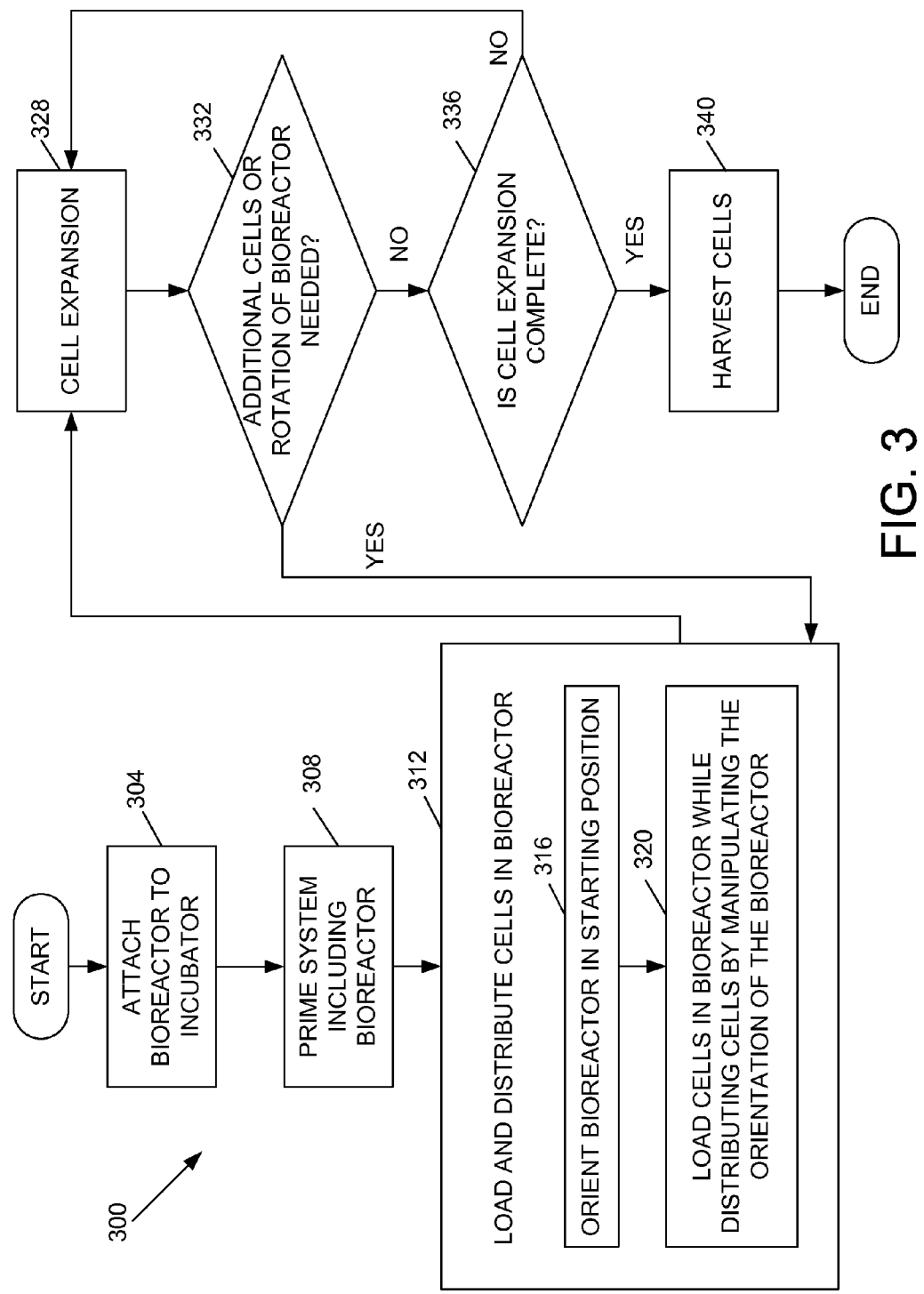
FIG. 3 is a flow chart of a method associated with loading and distributing cells in a cell expansion system.

Referring now to FIG. 3, a flow chart is shown that depicts a cell expansion process 300 associated with using CES 200, including the novel steps associated with loading and distributing cells in the bioreactor 100, as further described herein. To start the cell expansion process 300, at 304 a bioreactor 100 and any associated tubing and related structures are attached to the body 208 to provide an operable CES 200. Once attached to the body 208, the bioreactor 100 and its associated tubing and related structures are primed at 308 using an appropriate priming fluid, such as saline. At 312, cells are loaded and distributed in the bioreactor 100. The loading and distributing of cells in the bioreactor at 312 additionally includes orienting the bioreactor 100 in a starting position at 316, and then loading and distributing the cells in the bioreactor 100 at 320. Following loading and distributing cells in the bioreactor 100, the cells undergo expansion at 328. That is, the cells within the bioreactor 100 are allowed to grow and/or multiply. At 332, an assessment is made as to whether additional cells need to be added to the bioreactor 100 and/or whether the bioreactor 100 needs to be rotated to distribute cells within the bioreactor 100. If additional cells need to be loaded into the bioreactor 100 and/or if cells need to be distributed in the bioreactor 100, then the cell expansion process 300 returns to step 312. If cells do not need to be added and/or the bioreactor 100 does not need to be rotated, then at 336 an assessment is made as to whether the cell expansion process 328 is complete. As used herein, the cell expansion process is determined to be complete if a sufficient number of cells and/or change in cell characteristics has been achieved. If the cell expansion process 328 is complete, the cells are harvested at 340. If cell expansion process 328 is not complete, then the cell expansion process at 328 is allowed to continue.

Figure 4:
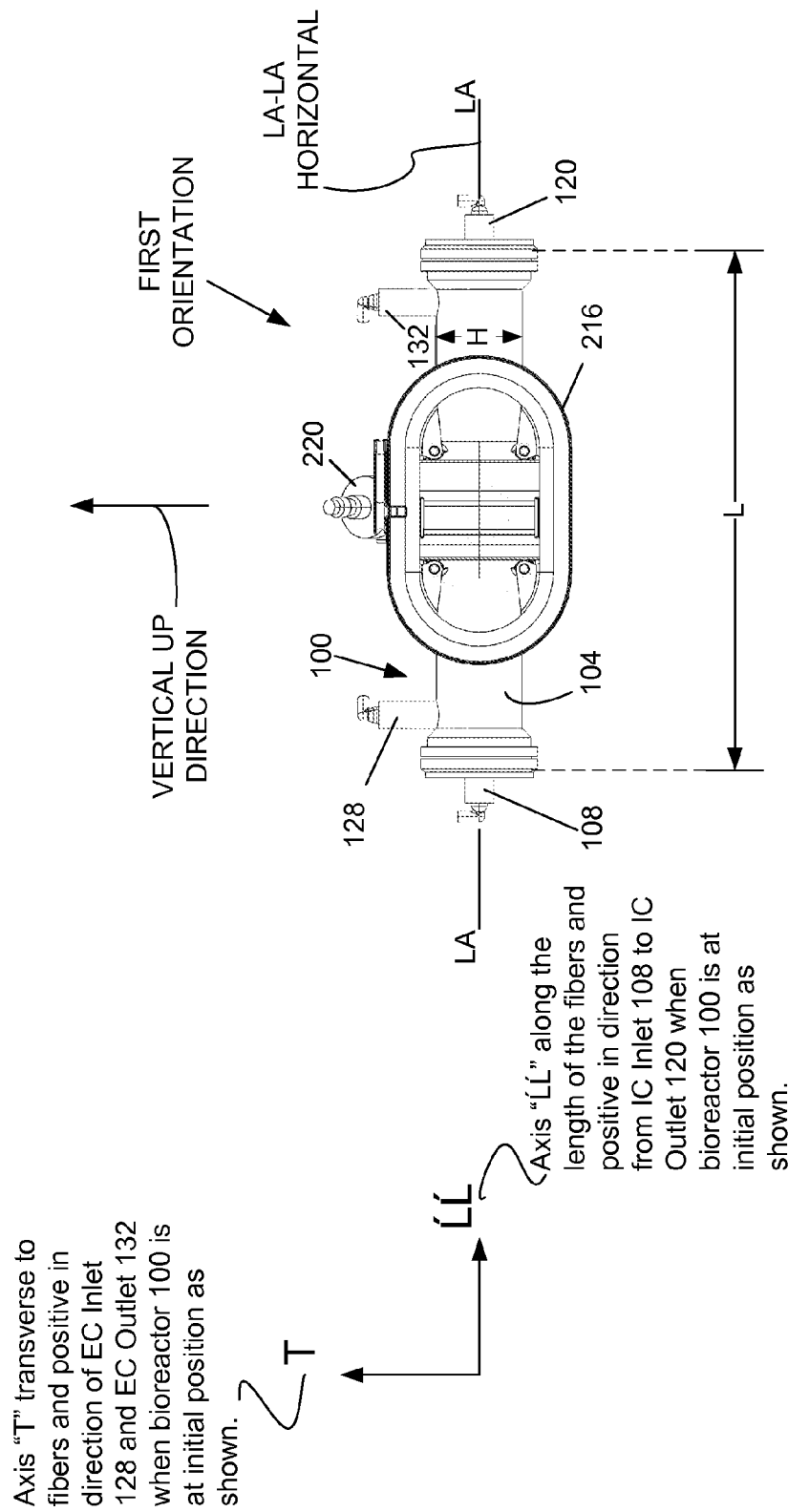
FIG. 4 is a front elevation view a bioreactor in a first orientation.

With further reference to the flow chart of FIG. 3, additional detail is now provided regarding loading and distributing cells in the bioreactor, as shown at 312. More particularly, at 316, the bioreactor 100 is oriented in its starting position. As best seen in FIG. 4, in at least one embodiment the bioreactor 100 is positioned horizontally to initiate loading and distributing cells in the bioreactor 100. That is, after the bioreactor 100 is primed at 308, at 316 the bioreactor 100 is oriented with its longitudinal axis LA-LA in a starting position, such as a substantially horizontal position. Thereafter, at 320 a plurality of cells is loaded into the bioreactor 100 while the bioreactor 100 is rotated (as described below) in a particular sequence to facilitate distribution of the cells through the bioreactor 100.

In at least one embodiment, cells may be loaded into the IC side of the bioreactor 100 (or into the hollow fibers 116 of the bioreactor 100) by causing flow of a media carrying the cells to pass from the IC inlet 108 to the EC outlet 132. In addition, cells may be loaded into the EC side of the bioreactor 100 (or to the exterior of the hollow fibers 116 of the bioreactor 100) by causing flow of a media carrying the cells to pass from the EC inlet 128 to the IC outlet 120.

To assist with determining the desired movements of the bioreactor 100 to facilitate improved distribution of cells within the bioreactor 100, a series of calculations were performed to calculate a basis for positioning the bioreactor 100. More particularly, by rotating the bioreactor 100, the influence of the acceleration due to gravity on a given cell (e.g., bone marrow cell) within the bioreactor 100 can be affected relative to the geometry of the bioreactor 100. To achieve a net impulse of zero on the cell, calculation of the impulse ("I") is performed to determine the change during rotation and counteract the impulse with the appropriate pause time at 0° and 270°.

To start, initial consideration is given to the acceleration experienced by a cell within the bioreactor 100. As a premise of the present invention, it is desirable to counteract the acceleration due to gravity ("g") on a given cell in the bioreactor 100 associated with distributing cells in the bioreactor 100. Accordingly, a rotation sequence for the bioreactor 100 is sought to achieve a net gravitational influence on a given cell of zero associated with loading and distributing cells in the bioreactor 100. Table 1 below provides a summary of gravitational acceleration influences along two axes, namely, the T and $\acute{L}\acute{L}$ axes as shown in FIG. 4, associated with the bioreactor 100.

TABLE 1

| Summary Table Of Acceleration Directions | | |
|---|---|---|
| Bioreactor Position | $a_T$ | $a_{\acute{L}\acute{L}}$ |
| At 0° | −(g is purely along T axis) | 0 |
| While Rotating 0° to 90° | −(a component of g is along T axis) | −(a component of g is along $\acute{L}\acute{L}$ axis) |
| While Rotating 90° to 180° | +(a component of g is along T axis) | −(a component of g is along $\acute{L}\acute{L}$ axis) |
| While Rotating 180° to 270° | +(a component of g is along T axis) | +(a component of g is along $\acute{L}\acute{L}$ axis) |

TABLE 1-continued

Summary Table Of Acceleration Directions

| Bioreactor Position | $a_T$ | $a_{LL}$ |
|---|---|---|
| Paused at 270° | 0 | +(g is purely along $\vec{LL}$ axis) |
| While Rotating 270° to 180° | +(a component of g is along T axis) | +(a component of g is along $\vec{LL}$ axis) |
| While Rotating 180° to 90° | +(a component of g is along T axis) | −(a component of g is along $\vec{LL}$ axis) |
| While Rotating 90° to 0° | −(a component of g is along T axis) | −(a component of g is along $\vec{LL}$ axis) |

Figure 5:
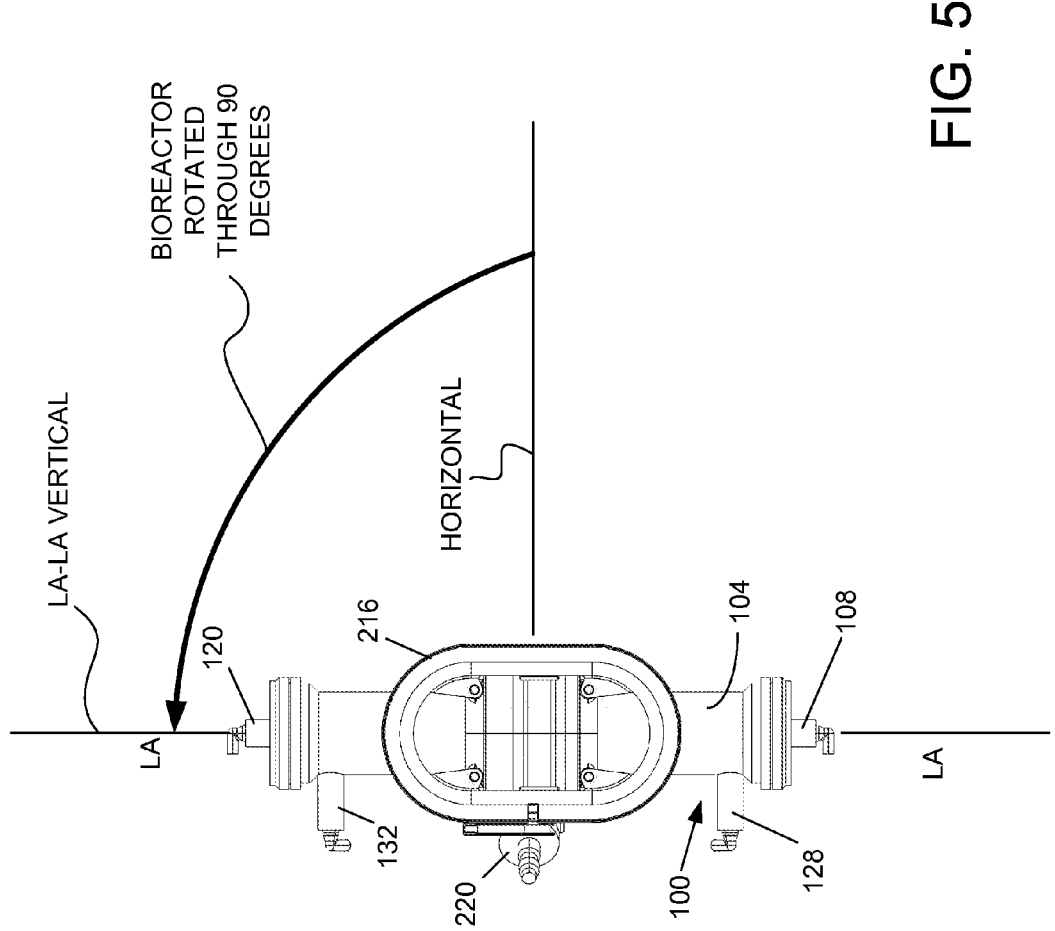
FIG. 5 is a front elevation view of the bioreactor of FIG. 4, wherein the bioreactor is shown rotated through 90° of rotation.
Figure 6:
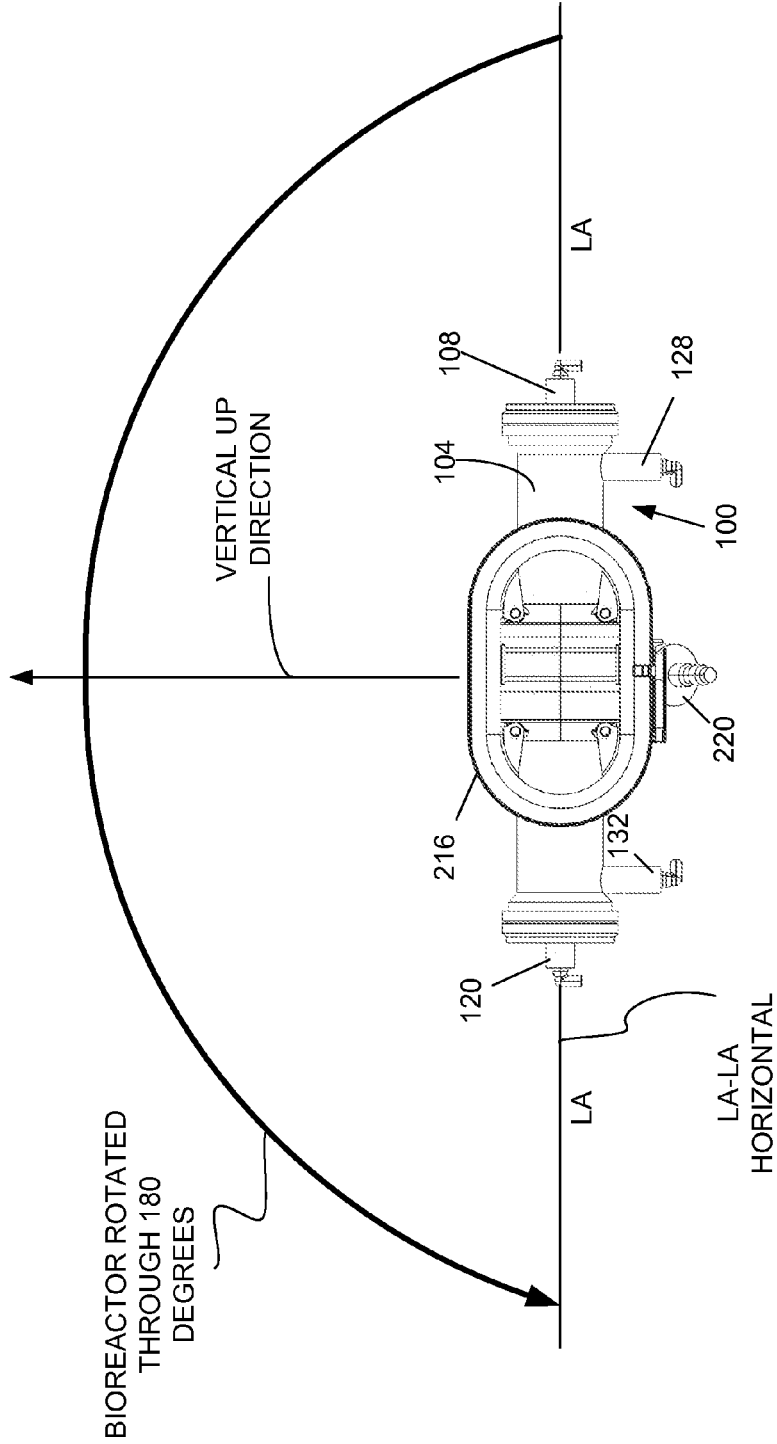
FIG. 6 is a front elevation view of the bioreactor of FIG. 4, wherein the bioreactor is shown rotated through 180° of rotation.
Figure 7:
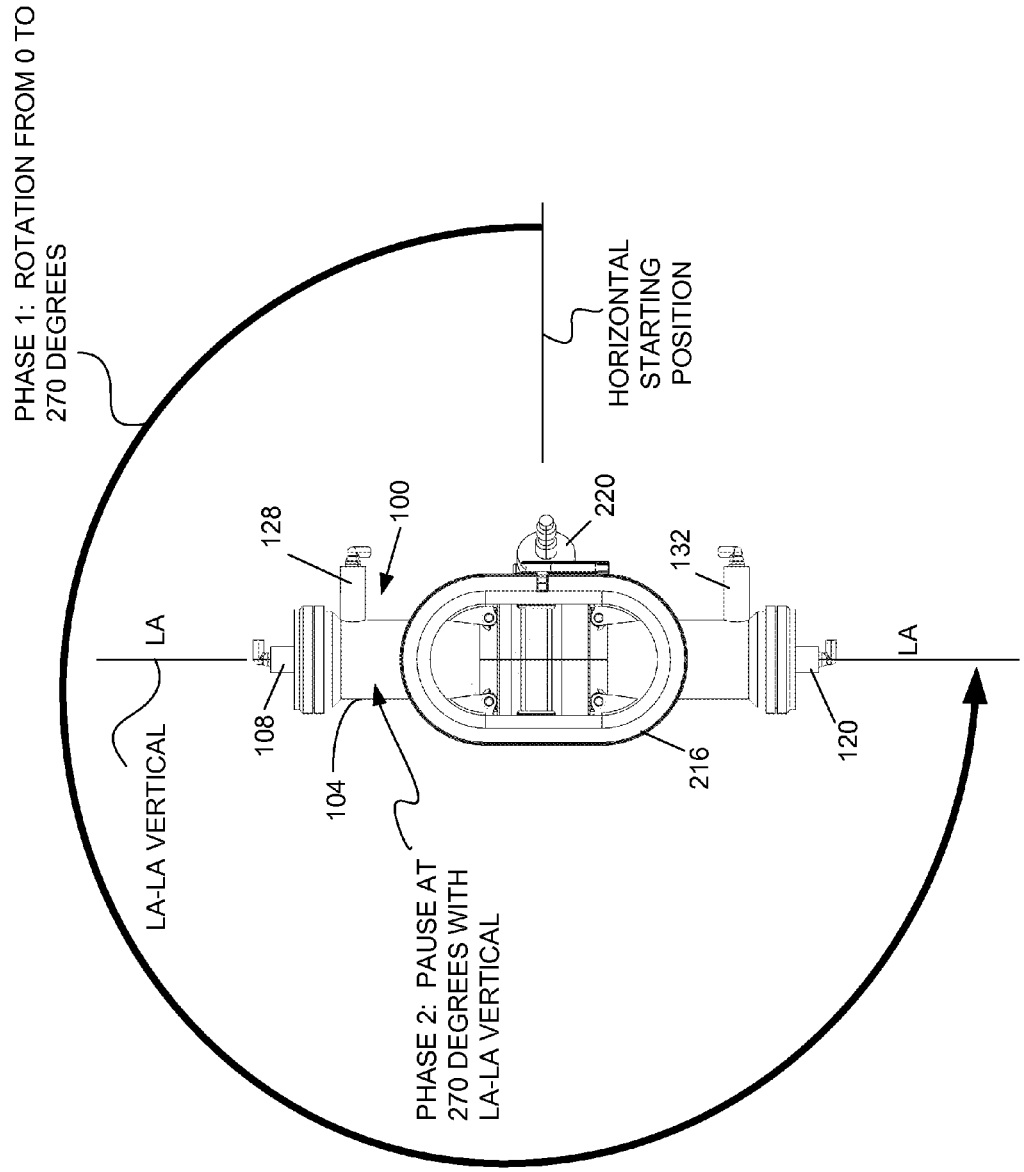
FIG. 7 is a front elevation view of the bioreactor of FIG. 4, wherein the bioreactor is shown rotated through 270° of rotation and to a second position.

For Table 1, a positive sign "+" indicates acceleration in the positive direction for the subject axis when the bioreactor is at the position or while rotating as shown in column 1; a negative sign "−" indicates acceleration in the negative direction for the subject axis when the bioreactor is at the position or while rotating as shown in column 1; and zero "0" indicates substantially no acceleration for the subject axis when the bioreactor is at the position as shown in column 1. Zero degrees (0°) is defined as the orientation of the bioreactor 100 when the longitudinal axis LA-LA is oriented horizontally with the EC inlet 128 and EC outlet 132 oriented upwards (as shown in FIG. 4); 90° is defined as vertical with the EC inlet 128 and EC outlet 132 oriented to the left (as shown in FIG. 5); 180° is defined as the longitudinal axis LA-LA oriented horizontally with the EC inlet 128 and EC outlet 132 oriented downwards (as shown in FIG. 6); and 270° is defined as vertical with the EC inlet 128 and EC outlet 132 oriented to the right (as shown in FIG. 7).

Accordingly, the impulse I is calculated as follows:
$\vec{I} = m \cdot \vec{a} \cdot_\Delta t$, where m is the mass of the cell and $_\Delta t$ is the time for which the acceleration is applied.
$I_T = m \cdot a_T \cdot_\Delta t$, where $I_T$ is the impulse in a direction traverse ("$\vec{T}$") to the longitudinal axis of the bioreactor.
$I_{LL} = m \cdot a_{LL} \cdot_\Delta t$, where $I_{LL}$ is the impulse in the longitudinal direction ("$\vec{LL}$") (i.e., parallel to the longitudinal axis LA-LA) of the bioreactor.

Pause at 0°:
$I_T = m \cdot (-g) \cdot t_{p,0°}$, where $t_{p,0°}$ is the pause time at 0° and "g" is the acceleration due to gravity $I_{LL} = m \cdot 0 \cdot t_{p,0°} = 0$ Rotation from 0° to 90°:

$$I_T = m \cdot a_{T,avg} \cdot \frac{90°}{\omega}$$

where $a_{T,avg}$ the average value of $a_T$ from 0° to 90°, and where $\omega$ is the radial velocity (degrees/second)

$$I_{LL} = m \cdot a_{LL,avg} \cdot \frac{90°}{\omega}$$

Alternatively, $$I_T = \int_0^{90/\omega} m \cdot a(t) dt$$

$$I_T = \int_0^{90/\omega} m \cdot (-g \cdot \cos(\omega t)) dt; \text{ substitute for } \theta$$

$$\theta = \omega t, \frac{d\theta}{dt} = \omega \ dt = \frac{d\theta}{\omega}$$

$$I_T = m \cdot -g \cdot \frac{1}{\omega} \int_0^{90} \cos\theta \cdot d\theta$$

-continued $$I_T = \frac{-m \cdot g}{\omega} \cdot [\sin\theta]_0^{90} = \frac{-m \cdot g}{\omega}[1 - 0] = \frac{-m \cdot g}{\omega}$$

Likewise, $$I_{LL} = \frac{-m \cdot g}{\omega} \cdot \int_0^{90} \sin\theta \cdot d\theta = \frac{-m \cdot g}{\omega} \cdot [-\cos\theta]_0^{90} = \frac{-m \cdot g}{\omega} \cdot [0 - -1]$$

$$= \frac{-m \cdot g}{\omega}$$

$$I_T = \frac{-m \cdot g}{\omega}$$

this will also be me same for rotation from 90° to 0°.

$$I_{LL} = \frac{-m \cdot g}{\omega}$$

Rotation from 90° to 180°:

$$I_T = \frac{-m \cdot g}{\omega} \cdot \int_{90}^{180} \cos\theta d\theta = \frac{-m \cdot g}{\omega} \cdot [\sin\theta]_{90}^{180} = \frac{-m \cdot g}{\omega} \cdot [0 - 1]$$

$$I_T = \frac{m \cdot g}{\omega}$$

$$I_{LL} = \frac{-m \cdot g}{\omega} \cdot \int_{90}^{180} \sin\theta d\theta$$

$$= \frac{-m \cdot g}{\omega} \cdot [-\cos\theta]_{90}^{180}$$

$$= \frac{m \cdot g}{\omega} \cdot [-1 - 0]$$

$$I_{LL} = \frac{-m \cdot g}{\omega}$$

Again, these win De the same as for 180° to 90°

Rotation from 180° to 270°

$$I_T = \frac{-m \cdot g}{\omega} \cdot \int_{180}^{270} \cos\theta \cdot d\theta = \frac{-m \cdot g}{\omega} \cdot [\sin\theta]_{180}^{270} = \frac{-m \cdot g}{\omega} \cdot [-1 - 0]$$

$$I_T = \frac{m \cdot g}{\omega}$$

-continued $$I_{LL}'' = \frac{-m \cdot g}{\omega} \cdot \int_{180}^{270} \sin\theta d\theta$$

$$= \frac{-m \cdot g}{\omega} \cdot [-\cos\theta]_{180}^{270}$$

$$= \frac{-m \cdot g}{\omega} \cdot [0-1]$$

$$I_{LL}'' = \frac{m \cdot g}{\omega}$$

Pause at 270°:

$I_T = m \cdot 0 \cdot t_{p,270°}$, where $t_{p,\,270°}$ is the pause time at 270°.
$I_{LL} = m \cdot g \cdot t_{p,270°}$

TABLE 2

Summary Table Using Impulse Values

| Bioreactor Position | $I_T$ | $I_{LL}$ |
|---|---|---|
| Example Initial Position: at 0° | — | — |
| While Rotating 0° to 90° | $\frac{-m \cdot g}{\omega}$ | $\frac{-m \cdot g}{\omega}$ |
| While Rotating 90° to 180° | $\frac{m \cdot g}{\omega}$ | $\frac{-m \cdot g}{\omega}$ |
| While Rotating 180° to 270° | $\frac{m \cdot g}{\omega}$ | $\frac{m \cdot g}{\omega}$ |
| Paused at 270° | 0 | $m \cdot g \cdot t_{p,270°}$ |
| While Rotating 270° to 180° | $\frac{m \cdot g}{\omega}$ | $\frac{m \cdot g}{\omega}$ |
| While Rotating 180° to 90° | $\frac{m \cdot g}{\omega}$ | $\frac{-m \cdot g}{\omega}$ |
| While Rotating 90° to 0° | $\frac{-m \cdot g}{\omega}$ | $\frac{-m \cdot g}{\omega}$ |
| Paused at 0° | $-m \cdot g \cdot t_{p,0°}$ | 0 |

Desire $\Sigma I_T = 0$, sum $I_T$ column and set equal to 0 to solve for $t_{p,0°}$.

Desire $\Sigma I_{LL} = 0$, sum $I_{LL}$ column and set equal to 0 to solve for $t_{p,270°}$.

$$\sum I_T = 0$$

$$= -m \cdot g \cdot t_{p,0°} + \frac{-m \cdot g}{\omega} + \frac{m \cdot g}{\omega} + \frac{m \cdot g}{\omega} + 0 +$$

$$\frac{m \cdot g}{\omega} + \frac{m \cdot g}{\omega} + \frac{-m \cdot g}{\omega}$$

$$\sum I_T = 0 = -m \cdot g \cdot t_{p,0°} + -2\frac{m \cdot g}{\omega} + 4\frac{m \cdot g}{\omega}$$

$$\sum I_T = 0 = -m \cdot g \cdot t_{p,0°} + 2\frac{m \cdot g}{\omega}$$

$$\cdot t_{p,0°} = \frac{2}{\omega}$$

$$t_{p,0°} = \frac{2}{\omega},$$

where $\omega$ is the constant angular velocity in radians/seconds $$\sum I_{LL} = 0$$

$$= 0 + \frac{-m \cdot g}{\omega} + \frac{-m \cdot g}{\omega} + \frac{m \cdot g}{\omega} + m \cdot g \cdot t_{p,270°} +$$

$$\frac{m \cdot g}{\omega} + \frac{-m \cdot g}{\omega} + \frac{-m \cdot g}{\omega}$$

$$\sum I_{LL} = 0 = m \cdot g \cdot t_{p,270°} + -4\frac{m \cdot g}{\omega} + 2\frac{m \cdot g}{\omega}$$

$$\sum I_{LL} = 0 = m \cdot g \cdot t_{p,270°} - 2\frac{m \cdot g}{\omega}$$

$$\frac{2}{\omega} = t_{p,270°}$$

$$t_{p,270°} = t_{p,0°} = \frac{2}{\omega},$$

where $\omega$ is the constant angular velocity in radians/second
For current constant angular velocity of 60° per second, $$\omega = \frac{60°}{\sec} \cdot \frac{2\pi \text{rad}}{360°} = \frac{\pi}{3} (\text{rad/sec})$$

$$t_{p,0°} = t_{p,270°} = \frac{2}{\omega} = \frac{2 \cdot 3}{\pi} = \frac{6}{\pi} \approx 1.91 \text{ seconds.}$$

In accordance with the foregoing calculations, a method of distributing cells in a bioreactor 100 includes manipulating the orientation of the bioreactor 100, such that a net impulse due to gravity acting on cells loaded into the bioreactor 100 is substantially zero. In accordance with at least one embodiment, the manipulation of the bioreactor comprises both rotating the bioreactor 100 and thereafter holding the bioreactor stationary for set periods of time. In accordance with at least one embodiment, the time for holding the bioreactor 100 stationary $t_p$ is approximately equal to the quantity $2\omega^{-1}$, wherein the angular velocity $\omega$ (rad/sec) is substantially constant for the periods when the bioreactor 100 is undergoing rotation. As those skilled in the art will appreciate, different angular velocities and pause times can be used.

Figure 8:
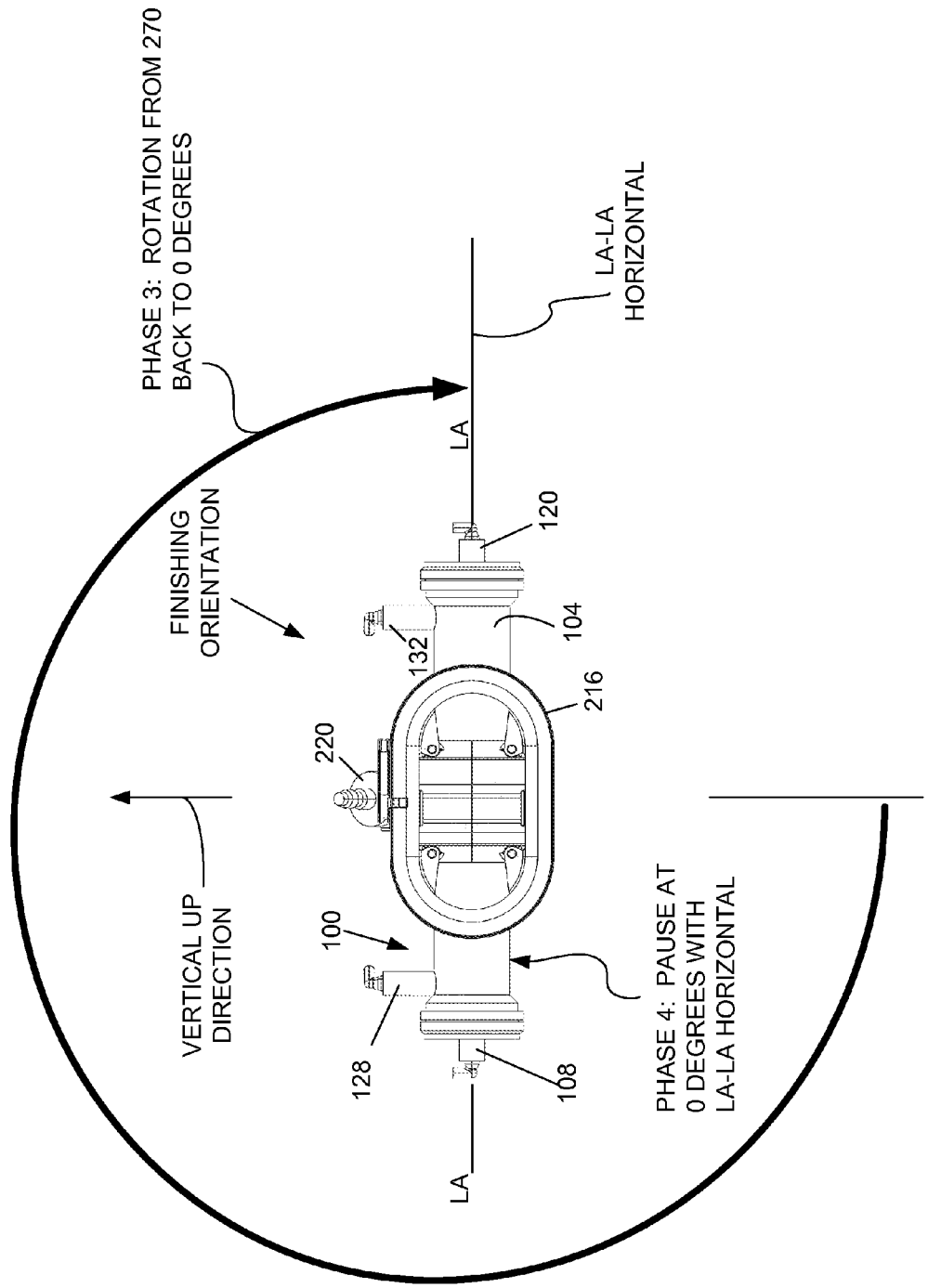
FIG. 8 is a front elevation view of the bioreactor of FIG. 4, wherein the bioreactor is shown rotated back to the initial starting position.

Referring again to FIG. 4, and in accordance with at least one embodiment, the orientation of the bioreactor 100 at the initial starting position is shown. Here, the longitudinal axis LA-LA of the bioreactor is substantially horizontal. While loading cells into the bioreactor 100, a sequence of manipulations is undertaken to mitigate the influence of gravity on the cells loaded into the bioreactor 100. More particularly, the bioreactor 100 is rotated though approximately 270° at a first angular velocity $\omega$. FIG. 5 illustrates the bioreactor 100 rotated through 90°. Continuing, FIG. 6 illustrates the bioreactor 100 having been rotated through 180°. Finally, FIG. 7 illustrates the bioreactor oriented at a second orientation, where the bioreactor 100 is held still for a period of time to allow the full influence of gravity to act in the positive direction of the LL axis. After the appropriate period of time for pausing the bioreactor 100, the bioreactor 100 is then rotated back to its original or initial starting position, as shown in FIG. 8.

As those skilled in the art will appreciate, more than one rotational direction is possible. In addition, more than one initial starting position is also possible provided a balancing of the influence of gravity on the cells loaded into the bioreactor 100 is achieved. Accordingly, the calculations, examples and discussion herein provide one or more possible configurations for manipulating the bioreactor 100 to reduce, minimize or eliminate the influence of gravity on cells and improve distribution of cells within the bioreactor. However, to the extent that other embodiments and variations are encompassed by the present disclosure, the calculations, description and figures are to be considered exemplary and non-limiting.

In accordance with at least one embodiment, the influence of gravity on cell distribution in the bioreactor 100 is controlled by the angular velocity applied to the bioreactor 100. More particularly, the rotational or angular velocity ω (rad/sec) is used to balance the net impulse due to gravity experienced by cells within the bioreactor 100. By way of example and not limitation, the bioreactor 100 is rotated as summarized below in Table 3.

TABLE 3

Summary Table Of Angular Velocities

| Bioreactor Position | Angular Velocity |
| --- | --- |
| Initial Position: −45° | 0 |
| While Rotating −45° to 0° | $\omega_1$ |
| While Rotating 0° to 180° | $\omega_2$ |
| While Rotating 180° to 225° | $\omega_1$ |
| Paused at 225° | 0 |
| While Rotating 225° to 180° | $\omega_1$ |
| While Rotating 180° to 0° | $\omega_2$ |
| While Rotating 0° to −45° | $\omega_1$ |
| Paused at −45° | 0 |

In the sequence of rotations summarized in Table 3, the bioreactor 100 is rotated from −45° to 225° and back, with the bioreactor 100 paused for a time $t_p$ at both −45° and 225°. More particularly, the bioreactor 100 is rotated from −45° to 0° at a rotational velocity $\omega_1$, and from 0° to 180° at a rotational velocity $\omega_2$. The bioreactor 100 is then rotated from 180° to 225° at rotational velocity $\omega_1$ and then paused for a prescribed time interval at 225°. After pausing at 225° the steps are reversed. Accordingly, from 225° to 180° the bioreactor 100 is rotated at rotational velocity $\omega_1$. Thereafter, the bioreactor 100 is rotated from 180° to 0° at a rotational velocity of $\omega_2$, and from 0° to −45° at a rotational velocity $\omega_1$. For this embodiment, $\omega_2$ can be determined as a function of $t_p$ and $\omega_1$:

$$\omega_2 = 4/((2/2^{0.5} \cdot t_p) + (4/\omega_1) \cdot ((2^{0.5}-1)/2^{0.5}))$$

As an example:
if $t_p = 1$ sec, and $\omega_1 = 30°/\text{sec}$ or $\pi/6$ rad/sec,
then $\omega_2 = 62.74°/\text{sec}$ or 1.095 rad/sec.

For the example directly above, it is observed that $\omega_2$ is approximately twice $\omega_1$.

As those skilled in the art will appreciate, the above-provided equation allows for solving for $\omega_2$ when $t_p = 0$ and $\omega_1$ is a known quantity. Accordingly, in at least one embodiment, a method of reducing a net impulse due to gravity acting on cells loaded into a bioreactor is provided, wherein a pause time of substantially zero is possible and the relationship of the angular velocities is described as:

$$\omega_2 = 4/((4/\omega_1) \cdot ((2^{0.5}-1)/2^{0.5}))$$

In addition to the foregoing, upon reviewing the intervals of application of the different angular velocities shown in Table 3, it can be seen that $\omega_2$ is applied for approximately 360° degrees of angular displacement, while $\omega_1$ is applied for half that, or approximately 180° of angular displacement.

In accordance with at least one embodiment, a method of distributing cells within a bioreactor 100 having a longitudinal axis LA-LA includes: initiating the loading and distributing of cells into the bioreactor 100 when the longitudinal axis LA-LA is substantially horizontal or angled at about 45° relative to horizontal; rotating the bioreactor 100 through a total of approximately 540° of angular displacement; and holding the bioreactor 100 still at a plurality of orientations. In at least one embodiment, the angular velocity of rotation is substantially the same for those intervals of time wherein the bioreactor is rotating. In at least one embodiment, the angular velocity of rotation of the bioreactor 100 is changed from a first angular velocity $\omega_1$ to a second angular velocity $\omega_2$ for portions of the time the bioreactor 100 is undergoing rotation.

Figure 9:
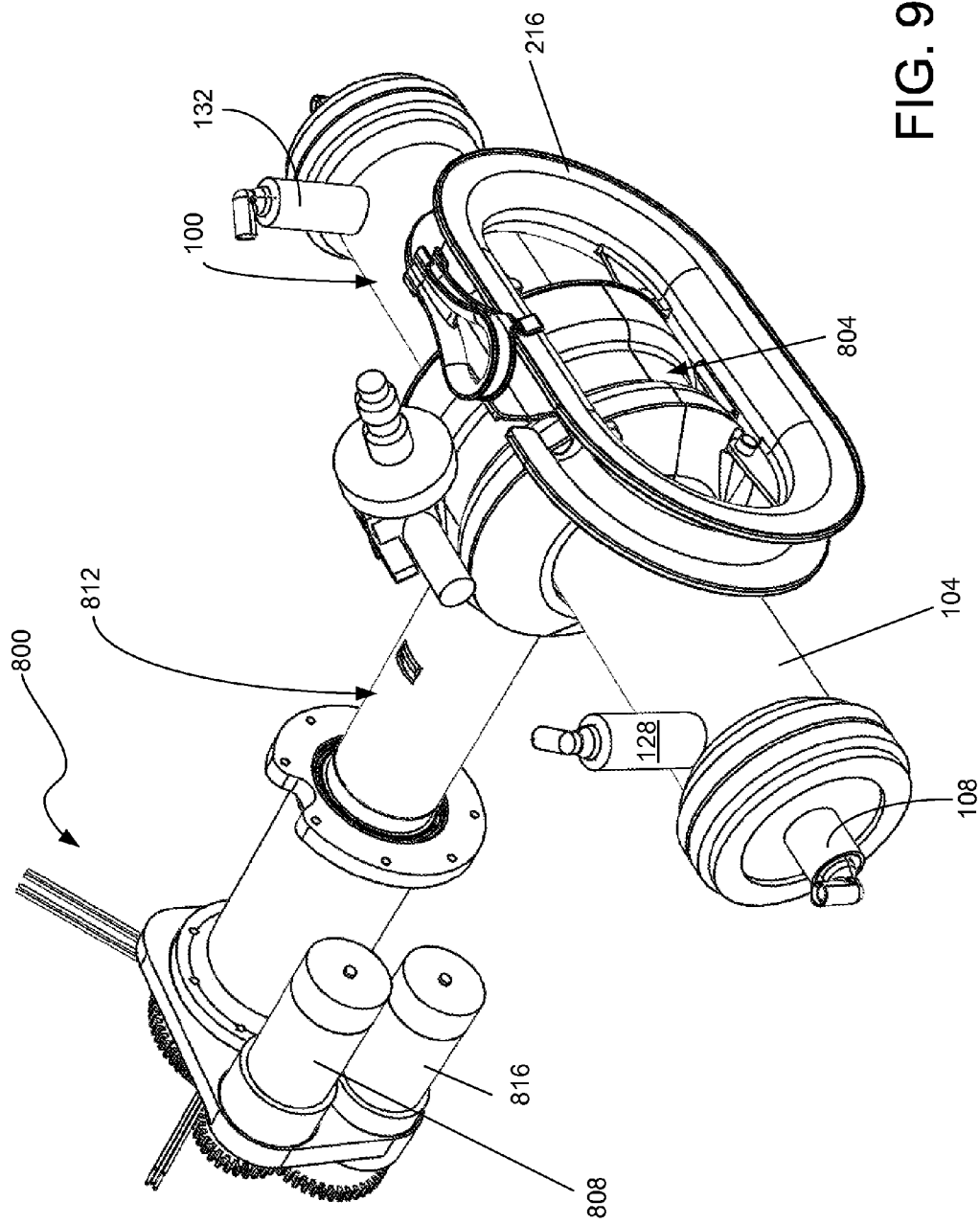
FIG. 9 is a perspective view of a bioreactor connected to a shaft assembly of a CES.
Figure 10:
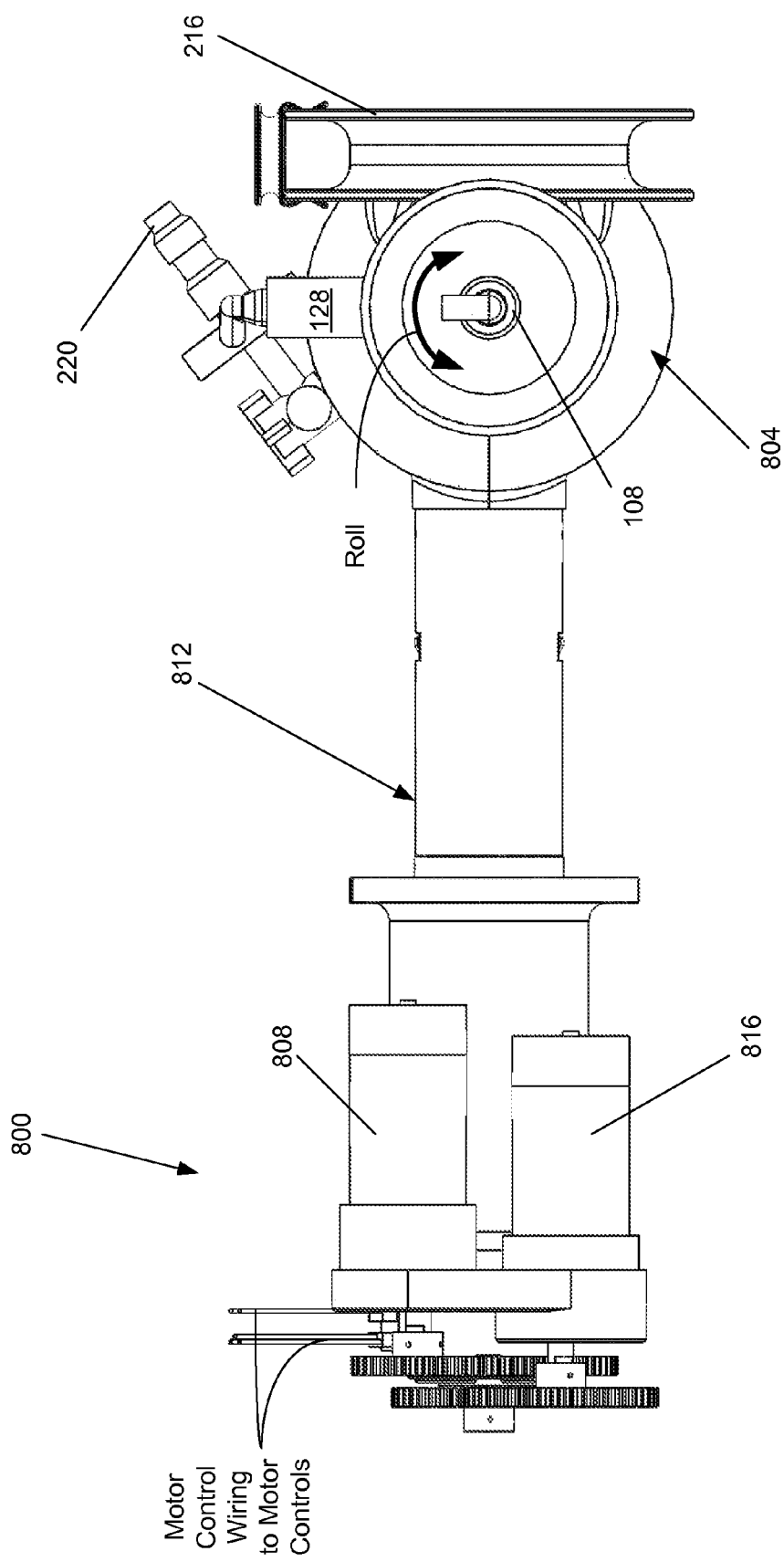
FIG. 10 is a side elevation view of the structures shown in FIG. 9.
Figure 11:
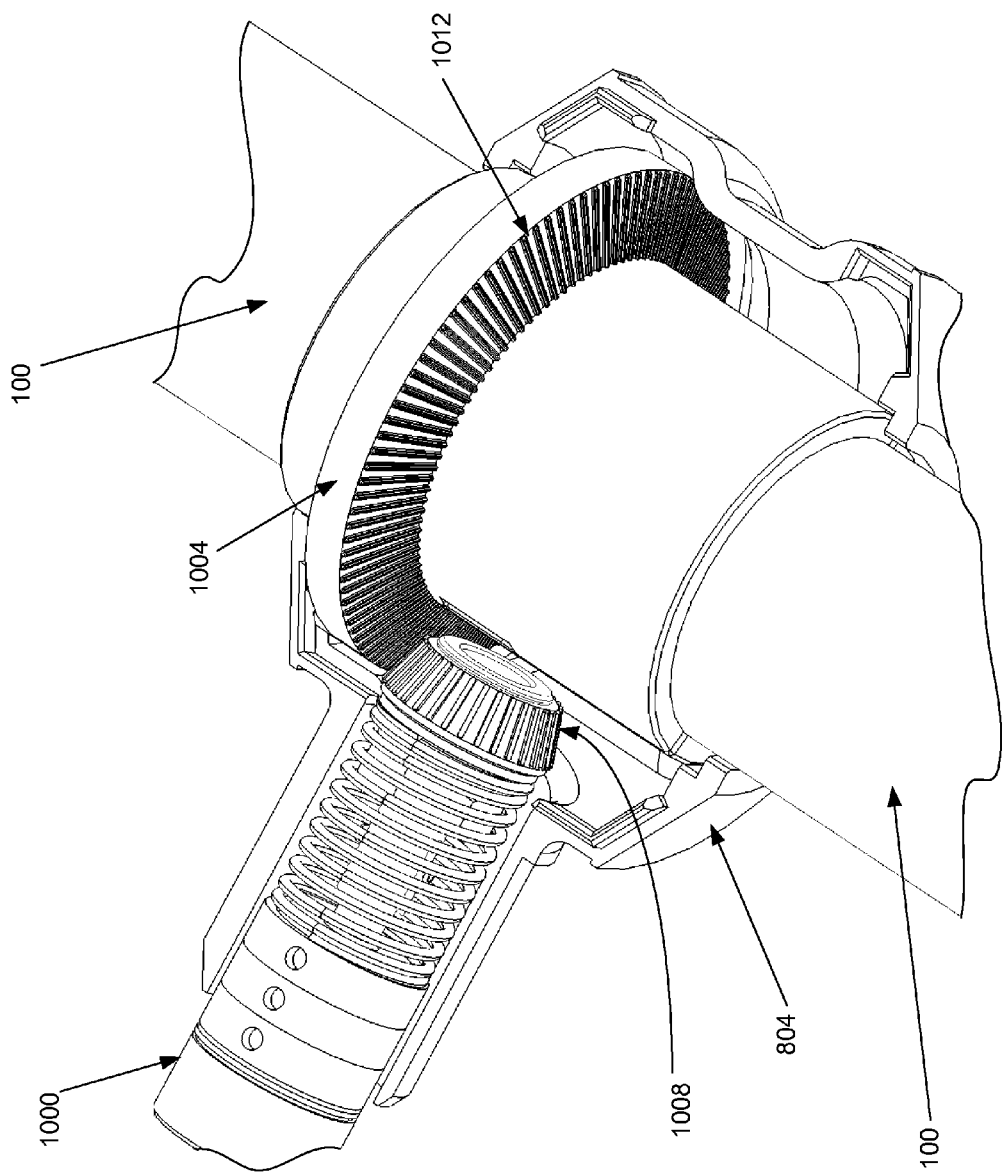
FIG. 11 is a detail perspective view of a fitting used to rotate a bioreactor around its longitudinal axis.

Referring now to FIGS. 9 and 10, different views of the bioreactor 100 are shown with the bioreactor 100 interconnected to a shaft assembly 800 by a chamber coupling 804. Motor 808 serves to rotate the outer shaft 812 around a rotation axis oriented through the shaft 812 and substantially perpendicular to the longitudinal axis of the bioreactor 100, thereby rotating the bioreactor 100 in a pitch mode as illustrated in FIGS. 5-8. Motor 816 serves to rotate an inner shaft (see FIG. 11) located within the outer shaft 812 to cause a roll fitting within the chamber coupling 804 to rotate the bioreactor 100 around its longitudinal axis LA-LA. As best seen in FIG. 11, an inner shaft 1000 includes structure for engaging a roll collar 1004 residing within the chamber coupling 804. The inner shaft member 1000 includes a beveled pinion 1008 residing at the very distal end of the inner shaft member 1000, and the beveled pinion 1008 contacts a sloped surface 1012 of the roll collar 1004 such that when the inner shaft member 1000 is rotated, the roll collar 1004 rotates, thereby causing the cell growth chamber 100 to rotate about its longitudinal axis LA-LA.

Figure 12:
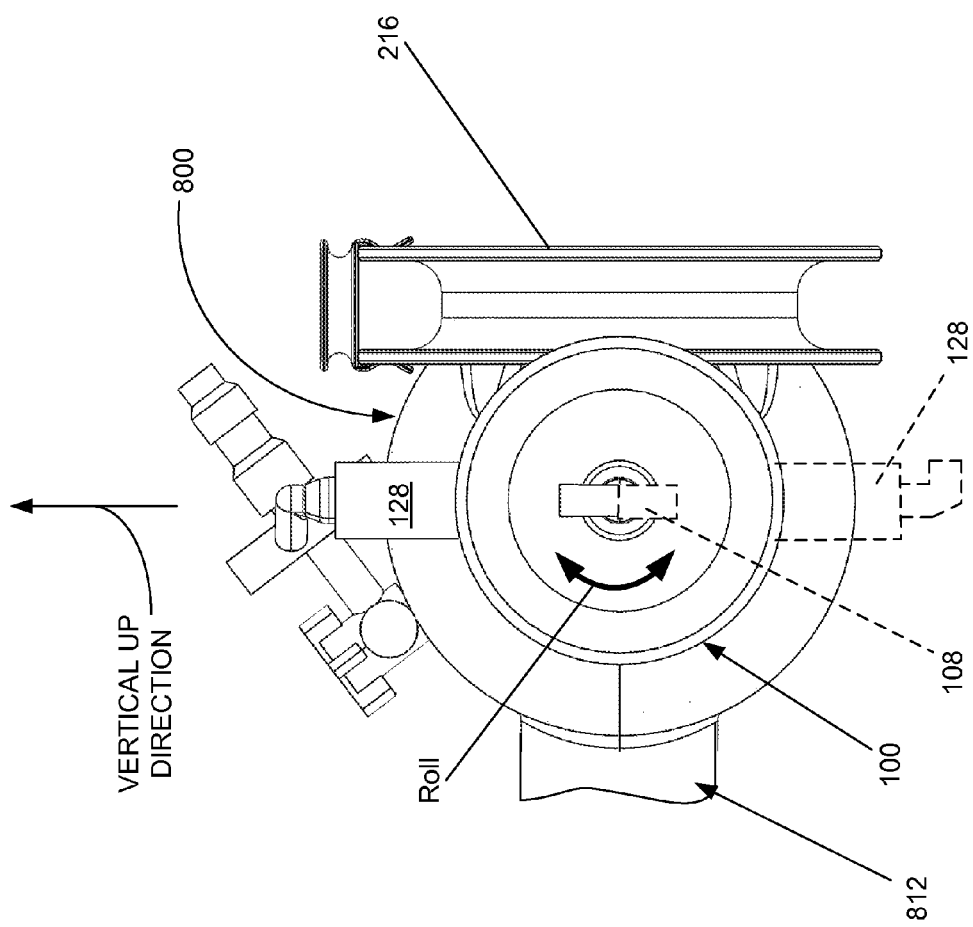
FIG. 12 is a side elevation view of a bioreactor illustrating rotation in roll.

With reference now to FIG. 12, an example of rotating the cell growth chamber in the roll mode is illustrated. In FIG. 12, a side elevation view of the cell growth chamber 100 is shown, wherein in a first roll position (shown with solid lines), the EC inlet port 128 is oriented vertically upwards. In a second roll position (shown with dashed lines), the EC inlet port 128 is oriented downwards. It is to be understood that the roll of the cell growth chamber 100 can be selectively controlled such that the cell growth chamber 100 can be rotated at any angle around its longitudinal axis. Periodic rotation of the cell growth chamber 100 in roll assists in preventing colonies of cells from settling during the cell loading and distribution process at step 312 depicted in the flow chart shown in FIG. 3.

In at least one embodiment, cells are loaded and distributed throughout the bioreactor 100 during a loading and distribution step that operates for greater than about 2 minutes of time. In at least one embodiment the loading and distribution step may operate for several minutes. During the loading and distribution step the bioreactor 100 undergoes a plurality of rotational sequences that are undertaken consecutively from the time loading of the cells is commenced until such time as substantially all of the cells have been loaded into the bioreactor 100 and its associated tubing.

In at least one embodiment, a bioreactor 100 is loaded with a plurality of cells while undergoing rotation such that a net impulse due to gravity acting on the plurality of cells is reduced relative to a net impulse due to gravity acting on the plurality of cells if the bioreactor 100 was not undergoing rotation. That is, the method comprises manipulating an orientation of the bioreactor such that an actual net impulse due to gravity acting on the plurality cells in the bioreactor is reduced relative to an avoided net impulse due to gravity acting on the plurality cells if the bioreactor was held in a stationary position.

In at least one embodiment, the bioreactor 100 is rotated through at least 180° of rotation to reduce the net impulse of gravity acting on the plurality of cells.

In at least one embodiment, the bioreactor 100 is rotated in a pitch mode to reduce the net impulse due to gravity acting on the plurality of cells, wherein an axis of rotation is oriented transversely to a longitudinal axis LA-LA of the bioreactor 100. In at least one embodiment, the bioreactor 100 is rotated in a roll mode to reduce the net impulse due to gravity acting on the plurality of cells, wherein an axis of rotation is oriented substantially parallel to a longitudinal axis LA-LA of the bioreactor 100. Here, the axis of rotation that is substantially parallel to the longitudinal axis LA-LA may be coincident with the longitudinal axis LA-LA.

In at least one embodiment, harvesting of cells from the bioreactor 100 is performed by manipulating the orientation of the bioreactor 100 as described herein. That is, the bioreactor 100 is rotated to reduce a net impulse due to gravity acting on the cells during the harvesting procedure. Such manipulation of the bioreactor during cell harvesting improves the collection efficiency of cells. In addition, such manipulation of the bioreactor during cell harvesting also improves the number of cells collected because the influence of gravity is overcome as the cells are washed from the bioreactor 100.

In at least one embodiment wherein cells are grown in a suspension and not adhered to the walls of hollow fibers in the bioreactor, the bioreactor can be continuously manipulated to reduce the influence due to gravity on cells residing with the bioreactor.

Various components may be referred to herein as "operably associated." As used herein, "operably associated" refers to components that are linked together in operable fashion, and encompasses embodiments in which components are linked directly, as well as embodiments in which additional components are placed between the two linked components.

The one or more present inventions may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The one or more present inventions, in various embodiments, include providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the one or more present inventions has been presented for purposes of illustration and description. The foregoing is not intended to limit the one or more present inventions to the form or forms disclosed herein. In the foregoing Detailed Description for example, various features of the one or more present inventions are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the one or more present inventions.

Moreover, though the description of the one or more present inventions has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of distributing a plurality of cells in a bioreactor of a cell expansion system, the method comprising:

loading the plurality of cells into an intracapillary side of the bioreactor, wherein the bioreactor comprises a plurality of hollow fibers;

manipulating an orientation of the bioreactor to reduce a net impulse due to gravity acting on the plurality of cells in the bioreactor, wherein the manipulating comprises determining a first angular velocity ($\omega_1$) for rotating the bioreactor;

determining a period of time ($t_p$) for holding the bioreactor substantially stationary;

calculating a second angular velocity ($\omega_2$) as a function of the first angular velocity ($\omega_1$) and the period of time ($t_p$), using:

$$\omega_2 = 4/((2/2^{0.5} \cdot t_p) + (4/\omega_1) \cdot ((2^{0.5}-1)/2^{0.5}));$$

rotating the bioreactor through a first angular displacement at the first angular velocity ($\omega_1$), the bioreactor rotating around a rotational axis in a first direction from a first orientation to a second orientation, wherein the rotational axis is substantially perpendicular to a longitudinal axis LA-LA of the bioreactor and the longitudinal axis LA-LA is parallel to the hollow fibers;

rotating the bioreactor through a second angular displacement at the second angular velocity ($\omega_2$), the bioreactor rotating around the rotational axis in the first direction from the second orientation to a third orientation, wherein the second angular velocity ($\omega_2$) is different from the first angular velocity ($\omega_1$);

rotating the bioreactor through a third angular displacement at the first angular velocity ($\omega_1$), the bioreactor rotating around the rotational axis in the first direction from the third orientation to a fourth orientation;

holding the bioreactor substantially stationary at the fourth orientation for the period of time ($t_p$) so that gravity influences the plurality of cells along an axis parallel to the longitudinal axis LA-LA; and rotating the bioreactor back around the rotational axis in a second direction to the third orientation at the first angular velocity ($\omega_1$), wherein the second direction is opposite of the first direction;

rotating the bioreactor around the rotational axis in the second direction from the third orientation to the second orientation at the second angular velocity ($\omega_2$); and rotating the bioreactor around the rotational axis in the second direction from the second orientation to the first orientation at the first angular velocity ($\omega_1$); and harvesting the plurality of cells.

2. The method of claim 1, wherein a total angular displacement associated with the manipulating is about 540°.

3. The method of claim 2, wherein the first orientation comprises a −45 degree position with respect to a horizontal position of the longitudinal axis LA-LA.

4. The method of claim 3, wherein the second orientation comprises a horizontal position of the longitudinal axis LA-LA.

5. The method of claim 4, wherein the third orientation comprises a 180 degree position with respect to a horizontal position of the longitudinal axis LA-LA.

6. The method of claim 5, wherein the fourth orientation comprises a 225 degree position with respect to a horizontal position of the longitudinal axis LA-LA.

7. The method of claim 1, wherein the harvesting the plurality of cells comprises manipulating an orientation of the bioreactor during the harvesting.

8. The method of claim 7, wherein the manipulating the orientation of the bioreactor during the harvesting improves a collection efficiency of the plurality of cells.

9. The method of claim 8, wherein the collection efficiency of the plurality of cells is improved by overcoming an influence of gravity as the plurality of cells is washed from the bioreactor.

10. The method of claim 1, wherein the loading the plurality of cells into the intracapillary side of the bioreactor comprises loading the plurality of cells into the plurality of hollow fibers of the bioreactor.

* * * * *